United States Patent
Leal et al.

(10) Patent No.: US 11,414,611 B2
(45) Date of Patent: Aug. 16, 2022

(54) METHOD OF PRODUCING A FUEL ADDITIVE

(71) Applicants: SABIC Global Technologies B.V., Bergen op Zoom (NL); Saudi Arabian Oil Company, Dhahran (SA)

(72) Inventors: Guillermo Leal, Riyadh (SA); Kareemuddin Mahaboob Shaik, Dhahran (SA); Naif Mohammed Al-Naddah Al-Otaibi, Riyadh (SA); Hiren Shethna, Dhahran (SA); Mohammed Bismillah Ansari, Riyadh (SA); Zhonglin Zhang, Dhahran (SA)

(73) Assignees: SABIC GLOBAL TECHNOLOGIES B.V., Bergen op Zoom (NL); SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 17/052,407

(22) PCT Filed: Apr. 18, 2019

(86) PCT No.: PCT/US2019/028099
§ 371 (c)(1),
(2) Date: Nov. 2, 2020

(87) PCT Pub. No.: WO2019/217050
PCT Pub. Date: Nov. 14, 2019

(65) Prior Publication Data
US 2021/0171848 A1     Jun. 10, 2021

Related U.S. Application Data

(60) Provisional application No. 62/667,683, filed on May 7, 2018.

(51) Int. Cl.
*C10L 1/185* (2006.01)
*C07C 4/04* (2006.01)
(Continued)

(52) U.S. Cl.
CPC .............. *C10L 1/1852* (2013.01); *C07C 4/04* (2013.01); *C07C 5/03* (2013.01); *C07C 5/05* (2013.01);
(Continued)

(58) Field of Classification Search
CPC ...... C10L 1/1852; C10L 1/1824; C10L 10/10; C07C 4/04; C07C 5/03; C07C 5/05; C07C 29/04; C07C 41/06
See application file for complete search history.

(56) References Cited

U.S. PATENT DOCUMENTS

| | | |
|---|---|---|
| 3,061,654 A | 10/1962 | Gensheimer et al. |
| 3,797,690 A | 3/1974 | Taylor et al. |

(Continued)

FOREIGN PATENT DOCUMENTS

| | | |
|---|---|---|
| CA | 2018524 A1 | 12/1990 |
| CN | 1044804 C | 8/1999 |

(Continued)

OTHER PUBLICATIONS

International Search Report for International Application No. PCT/IB2019/059984; International Filing Date Nov. 20, 2019; dated Feb. 21, 2020; 5 pages.

(Continued)

*Primary Examiner* — Latosha Hines
(74) *Attorney, Agent, or Firm* — Cantor Colburn LLP

(57) ABSTRACT

A method of producing a fuel additive includes passing a feed stream comprising C4 hydrocarbons through a methyl tertiary butyl ether unit producing a first process stream; passing the first process stream through a selective butadiene (Continued)

hydrogenation unit transforming greater than or equal to 90% by weight of the butadiene to 1-butene and 2-butene, preferably greater than or equal to 93%, preferably, greater than or equal to 94%, more preferably, greater than or equal to 95% producing a second process stream; passing the second process stream through a hydration unit producing a third process stream and the fuel additive; passing the third process stream through a total hydrogenation unit producing a hydrogenated stream; and passing the hydrogenated stream to a cracker unit.

20 Claims, 1 Drawing Sheet

(51) Int. Cl.
| | |
|---|---|
| *C07C 5/03* | (2006.01) |
| *C07C 5/05* | (2006.01) |
| *C10L 1/182* | (2006.01) |
| *C10L 10/10* | (2006.01) |
| *C07C 29/04* | (2006.01) |
| *C07C 41/06* | (2006.01) |

(52) U.S. Cl.
CPC .............. *C07C 29/04* (2013.01); *C07C 41/06* (2013.01); *C10L 1/1824* (2013.01); *C10L 10/10* (2013.01)

(56) References Cited

U.S. PATENT DOCUMENTS

| | | | |
|---|---|---|---|
| 3,849,082 A | 11/1974 | Kozlowski et al. | |
| 3,912,463 A | 10/1975 | Kozlowski et al. | |
| 4,334,890 A | 6/1982 | Kochar et al. | |
| 4,336,046 A | 6/1982 | Schorre et al. | |
| 4,356,339 A | 10/1982 | Imaizumi et al. | |
| 4,408,085 A | 10/1983 | Gottlieb et al. | |
| 4,423,251 A | 12/1983 | Pujado et al. | |
| 4,455,445 A | 6/1984 | Neuzil et al. | |
| 4,499,313 A | 2/1985 | Okumura et al. | |
| 4,540,831 A | 9/1985 | Briggs | |
| 4,773,968 A | 9/1988 | O'Connell et al. | |
| 4,783,555 A | 11/1988 | Atkins | |
| 4,797,133 A * | 1/1989 | Pujado ................ C07C 7/14891 | |
| | | | 44/449 |
| 4,927,977 A | 5/1990 | Child et al. | |
| 5,227,553 A | 7/1993 | Polanek et al. | |
| 5,254,748 A | 10/1993 | Hensley et al. | |
| 5,382,707 A | 1/1995 | Rubin et al. | |
| 5,523,502 A | 6/1996 | Rubin | |
| 5,563,299 A | 10/1996 | Paludetto et al. | |
| 5,628,880 A | 5/1997 | Hearn et al. | |
| 5,672,795 A | 9/1997 | Vora et al. | |
| 5,877,365 A * | 3/1999 | Chodorge ................ C07C 6/04 | |
| | | | 585/329 |
| 5,898,091 A | 4/1999 | Chodorge et al. | |
| 5,955,640 A | 9/1999 | Paludetto et al. | |
| 7,227,047 B2 | 6/2007 | Risch et al. | |
| 7,473,812 B2 | 1/2009 | Peters et al. | |
| 7,485,761 B2 | 2/2009 | Schindler et al. | |
| 8,124,572 B2 | 2/2012 | Miller | |
| 8,395,007 B2 | 3/2013 | Wright et al. | |
| 8,999,013 B2 | 4/2015 | Xu et al. | |
| 9,187,388 B2 | 11/2015 | Arjah et al. | |
| 9,611,192 B2 | 4/2017 | Digiulio | |
| 10,774,020 B2 | 9/2020 | Di Girolamo et al. | |
| 2002/0169346 A1 | 11/2002 | Commereuc et al. | |
| 2003/0158429 A1 | 8/2003 | Albiez et al. | |
| 2004/0171891 A1 * | 9/2004 | Scholz .................... C07C 29/04 | |
| | | | 568/899 |
| 2005/0288534 A1 * | 12/2005 | Fernandez .............. C07C 29/04 | |
| | | | 568/894 |
| 2007/0149839 A1 * | 6/2007 | Rix ........................... C07C 7/04 | |
| | | | 585/664 |
| 2007/0265483 A1 | 11/2007 | Himelfarb | |
| 2008/0146858 A1 | 6/2008 | Elomari et al. | |
| 2008/0312481 A1 | 12/2008 | Leyshon | |
| 2009/0193710 A1 * | 8/2009 | Xiong ..................... C10L 1/023 | |
| | | | 44/449 |
| 2011/0040133 A1 | 2/2011 | Vermeiren et al. | |
| 2011/0230632 A1 * | 9/2011 | Abhari .................... C10G 9/36 | |
| | | | 526/335 |
| 2012/0117862 A1 | 5/2012 | Xu | |
| 2012/0283492 A1 | 11/2012 | Dalemat et al. | |
| 2013/0072732 A1 | 3/2013 | Breuil et al. | |
| 2013/0104449 A1 | 5/2013 | Xu et al. | |
| 2013/0331620 A1 | 12/2013 | Abhari | |
| 2014/0039226 A1 | 2/2014 | Xu et al. | |
| 2014/0142350 A1 | 5/2014 | Weiner et al. | |
| 2015/0225320 A1 | 8/2015 | Shaik et al. | |
| 2015/0322181 A1 | 11/2015 | Kim et al. | |
| 2016/0326079 A1 | 11/2016 | Lee et al. | |
| 2017/0073289 A1 | 3/2017 | Leal et al. | |
| 2017/0198231 A1 | 7/2017 | Xu et al. | |
| 2017/0253540 A1 | 9/2017 | Hofel et al. | |
| 2020/0157450 A1 | 5/2020 | Leal et al. | |
| 2021/0002185 A1 | 1/2021 | Leal et al. | |
| 2021/0024837 A1 | 1/2021 | Leal et al. | |
| 2021/0024843 A1 | 1/2021 | Leal et al. | |
| 2021/0155862 A1 | 5/2021 | Leal et al. | |
| 2021/0214290 A1 | 7/2021 | Ansari et al. | |
| 2021/0246088 A1 | 8/2021 | Leal et al. | |

FOREIGN PATENT DOCUMENTS

| | | | |
|---|---|---|---|
| CN | 1506344 A | 6/2004 | |
| CN | 101279879 A | 10/2008 | |
| CN | 102070391 A | 5/2011 | |
| CN | 105585411 A | 5/2016 | |
| CN | 106608791 A | 5/2017 | |
| CN | 102372573 A | 3/2021 | |
| EP | 0063813 B1 | 11/1982 | |
| EP | 0102840 B1 | 3/1984 | |
| EP | 0253679 | 1/1988 | |
| EP | 0253679 A2 * | 1/1988 | .............. C07C 29/04 |
| EP | 0605822 A1 | 7/1994 | |
| GB | 1374368 | 8/1972 | |
| JP | S5920232 A | 2/1984 | |
| RU | 2470905 C1 | 12/2012 | |
| WO | 9011268 | 10/1990 | |
| WO | 9732838 A1 | 9/1997 | |
| WO | 0043336 A1 | 7/2000 | |
| WO | 0146095 A1 | 6/2001 | |
| WO | 2006113191 A2 | 10/2006 | |
| WO | 2007024733 A2 | 3/2007 | |
| WO | 2012095744 A2 | 7/2012 | |
| WO | 2014153570 A2 | 9/2014 | |
| WO | 2014160825 A1 | 10/2014 | |
| WO | 2015089005 A1 | 6/2015 | |
| WO | 2015123026 A1 | 8/2015 | |
| WO | 2019207477 | 10/2019 | |

OTHER PUBLICATIONS

Written Opinion for International Application No. PCT/IB2019/059984; International Filing Date Nov. 20, 2019; dated Feb. 21, 2020; 8 pages.
International Search Report for International Application No. PCT/US2019/028099; International Filing Date Apr. 18, 2019; dated Jun. 26, 2019; 6 pages.
Streich et al.; "Secure the Best Benefits from C4 Hydrocarbon Processing—Part 1: Separation Sequences" Hydrocarbon Processing: Process Engineering and Optimization; 2016; 6 pages.
Written Opinion for International Application No. PCT/US2019/028099; International Filing Date Apr. 18, 2019 dated Jun. 26, 2019; 13 pages.
Bodas et al.; U.S. Appl. No. 17/292,261; entitled "Process and System for Producing Ethylene and At Least One of Butanol and an Alkyl Tert-Butyl Ether"; filed with USPTO on May 7, 2021.

(56) References Cited

OTHER PUBLICATIONS

International Search Report for International Application No. PCT/IB2020/051908; International Filing Date Mar. 5, 2020; dated May 29, 2020; 6 pages.
Leal et al. U.S. Appl. No. 17/436,753, entitled "Method of Producing a Fuel Additive", filed with the USPTO on Sep. 7, 2021.
Written Opinion for International Application No. PCT/IB2020/051908; International Filing Date Mar. 5, 2020 Date of Mailing May 29, 2020; 9 pages.
Bender et al.; "Selective Hydrogenation in Steam Cracking"; 21st Annual Saudi-Japan Symposium; Catalysts in Petroleum Refining & Petrochemicals; King Fahd University of Petroleum & Minerals; 2011; Abstract only; pp. 1-3.
Brockwell et al.; "Synthesize ethers"; Hydrocarbon Processing, vol. 70, No. 9; 1991; pp. 133-141.
International Search Report for International Application No. PCT/IB2019/052177; International Filing Date Mar. 18, 2019; dated Jun. 26, 2019; 3 pages.
International Search Report for International Application No. PCT/IB2019/052178; International Filing Date Mar. 18, 2019; dated Jun. 26, 2019; 6 pages.
International Search Report for International Application No. PCT/IB2019/053697; International Filing Date May 6, 2019; dated Aug. 28, 2019; 11 pages.
International Search Report for International Application No. PCT/IB2019/057784; International Filing Date Sep. 16, 2019; dated Jan. 7, 2020; 5 pages.
International Search Report for International Application No. PCT/US2019/026985; International Filing Date Apr. 11, 2019; dated May 27, 2019; 6 pages.
International Search Report for International Application No. PCT/US2019/028092; International Filing Date Apr. 18, 2019; dated Jun. 26, 2019; 6 pages.
International Search Report; International Application No. PCT/IB2018/055647; International Filing Date: Jul. 27, 2018 dated Oct. 30, 2018; 6 pages.
Izquierdo et al.; "Equilibrium Constants for Methyl tert-Butyl Ether Liquid-Phas Synthesis"; J. Chern. Eng. Data, vol. 37; 1992; pp. 339-343.
Kalamaras et al.; "SuperButol—A novel high-octane gasoline blending component"; Fuel, vol. 195; 2017; pp. 165-173.
Written Opinion for International Application No. PCT/IB2019/052177; International Filing Date Mar. 18, 2019 dated Jun. 26, 2019; 9 pages.
Written Opinion for International Application No. PCT/IB2019/052178; International Filing Date Mar. 18, 2019 dated Jun. 26, 2019; 9 pages.
Written Opinion for International Application No. PCT/IB2019/053697; International Filing Date May 6, 2019; dated Aug. 28, 2019; 9 pages.
Written Opinion for International Application No. PCT/IB2019/057784; International Filing Date Sep. 16, 2019; dated Jan. 7, 2020; 7 pages.
Written Opinion for International Application No. PCT/US2019/026985; International Filing Date Apr. 11, 2019 dated May 27, 2019; 7 pages.
Written Opinion for International Application No. PCT/US2019/028092; International Filing Date Apr. 18, 2019 dated Jun. 26, 2019; 9 pages.
Written Opinion; International Application No. PCT/IB2018/055647; International Filing Date: Jul. 27, 2018; dated Oct. 30, 2018; 11 pages.

* cited by examiner

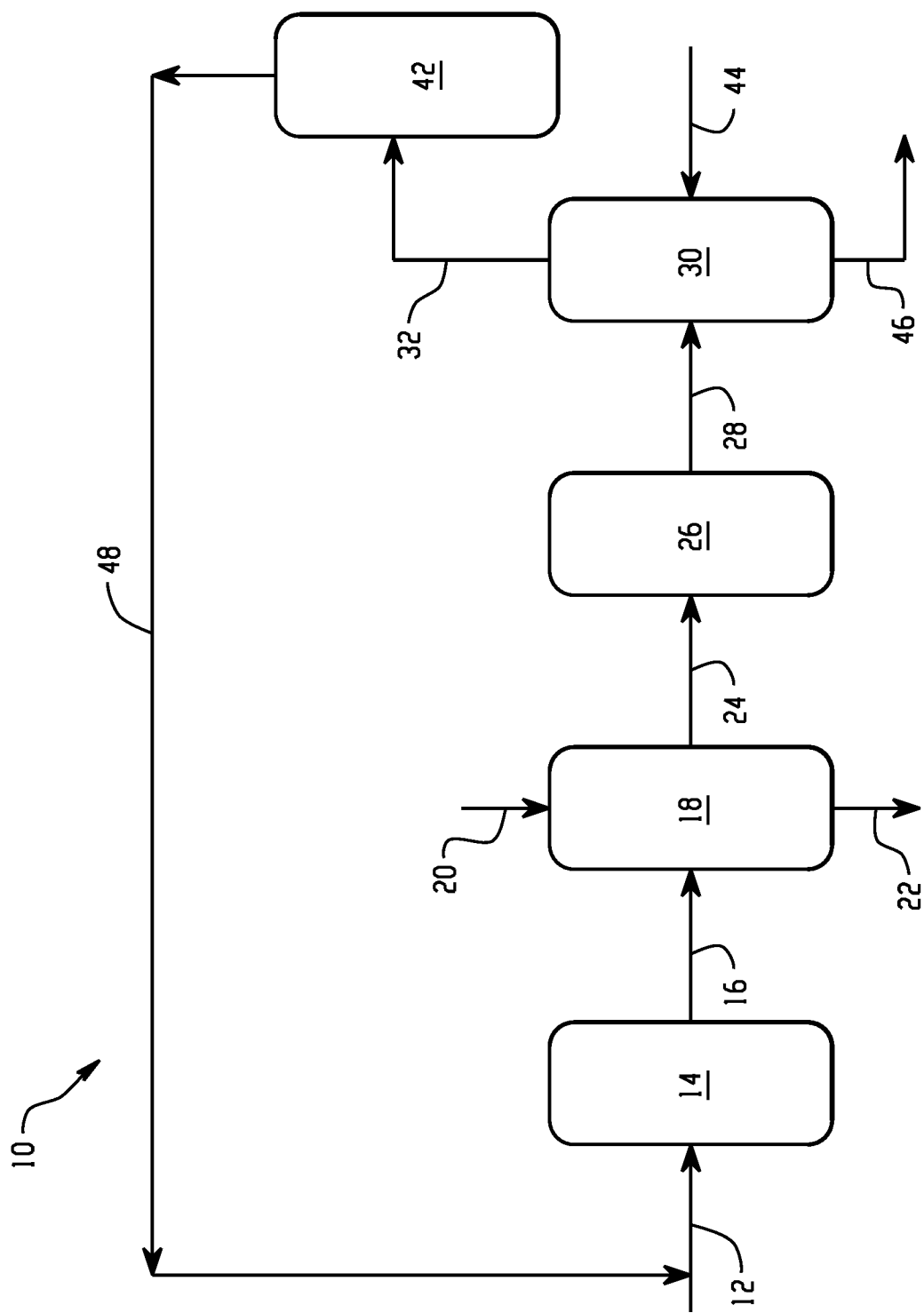

METHOD OF PRODUCING A FUEL ADDITIVE

CROSS REFERENCE TO RELATED APPLICATIONS

This application is a National Stage application of PCT/US2019/028099, filed Apr. 18, 2019, which is incorporated herein by reference in its entirety, and which claims the benefit of U.S. Provisional Application No. 62/667,683, filed May 7, 2018.

BACKGROUND

Commercial gasoline, which is fuel for internal combustion engines, is a refined petroleum product that is typically a mixture of hydrocarbons (base gasoline), additives, and blending agents. Additives and blending agents are added to the base gasoline to enhance the performance and the stability of gasoline, for example octane boosters.

When used in high compression internal combustion engines, gasoline has the tendency to "knock." Knocking occurs when combustion of the air/fuel mixture in the cylinder does not start off correctly in response to ignition because one or more pockets of air/fuel mixture pre-ignite outside the envelope of the normal combustion front. Anti-knocking agents, also known as octane boosters, reduce the engine knocking phenomenon, and increase the octane rating of the gasoline.

Hydrocarbon cracking processes are important conversion processes used in petroleum refineries. For example, fluid catalytic cracking (FCC) is widely used to convert the high-boiling, high-molecular weight hydrocarbon fractions of petroleum crude oils to more valuable gasoline, olefinic gases, and other products. Thermal cracking of naphtha and gas oil is also widely used in the petrochemical industry to produce a variety of olefins and aromatics. For example, hydrocarbon feed stocks can be mixed with steam and subjected to elevated temperatures (e.g., 700-900° C.) in a steam cracker furnace wherein the feed stock components are cracked into various fractions. The effluent of the steam cracker can contain a gaseous mixture of hydrocarbons, for example, saturated and unsaturated olefins and aromatics (C1-C35). The effluent can then be separated into individual olefins (for example, ethylene, propylene and C4's) and pyrolysis gasoline. Recycle streams of crude hydrocarbons are often formed as by-products during these cracking processes.

The presence of isobutylene, butadiene, 1-butene, 2-butene, and other components within the crude hydrocarbon streams can allow for the formation of valuable alcohols and fuel additives. However, the conversion of crude hydrocarbon streams to fuel additive products can often be inefficient and costly. Furthermore, the final product specifications for such alcohols can be undesirable and can fail to meet market quality requirements. For example, alcohol products can have high levels of impurities, high Reid vapor pressures, e.g., greater than 2.0 pounds per square inch (psi) (greater than 10 kilopascals, greater than 12 kilopascals, greater than 13 kilopascals, greater than 14 kilopascals), and low octane numbers (e.g., 82 Research Octane Number (RON)), all of which correlate with poor product quality. Any improvement in these specifications and/or the efficiency of the process can provide a more valuable fuel additive product.

Thus, there is a need for an efficient method of producing fuel additives that can make use of crude hydrocarbon streams and produce final products with low impurities and high performance specifications.

SUMMARY

Disclosed, in various embodiments, are methods of producing fuel additives.

A method of producing a fuel additive comprises: passing a feed stream comprising C4 hydrocarbons through a methyl tertiary butyl ether unit producing a first process stream; passing the first process stream through a selective butadiene hydrogenation unit transforming greater than or equal to 90% by weight of the butadiene to 1-butene and 2-butene, preferably greater than or equal to 93%, preferably, greater than or equal to 94%, more preferably, greater than or equal to 95% producing a second process stream; passing the second process stream through a hydration unit producing a third process stream and the fuel additive; passing the third process stream through a total hydrogenation unit producing a hydrogenated stream; and passing the hydrogenated stream to a cracker unit.

A method of producing a fuel additive comprises: passing a feed stream comprising hydrocarbons through a cracker unit producing a cracked stream; passing the cracked stream through a methyl tertiary butyl ether unit to produce a first process stream, wherein methanol and isobutylene are present in the methyl tertiary butyl ether unit in a molar ratio of one mole of isobutylene to 0.1 mole to 5 moles of methanol; withdrawing a methyl tertiary butyl ether product from the methyl tertiary butyl ether unit; passing the first process stream through a selective butadiene hydrogenation unit to produce a second process stream; passing the second process stream through a hydration unit producing a third process steam, wherein a temperature within the hydration unit is 30° C. to 190° C., a pressure within the hydration unit is 500 kiloPascals to 20,000 kiloPascals, and wherein greater than or equal to 0.10% of any butene present in the third process stream is converted to butanol within the hydration unit; withdrawing a fuel additive product from the hydration unit, wherein the fuel additive product comprises 1-butanol, 2-butanol, tert-butyl alcohol, di-isobutene, or a combination thereof; passing the third process stream through a total hydrogenation unit producing a hydrogenated process stream; and recycling the hydrogenated process stream to a cracker unit.

These and other features and characteristics are more particularly described below.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

The FIGURE is a schematic diagram representing a unit sequence for producing fuel additives.

DETAILED DESCRIPTION

Disclosed herein is an efficient method of producing fuel additives that can make use of crude hydrocarbon streams and produce final products with low impurities and high performance specifications. For example, the method disclosed herein can provide a unique sequence of unit operations that converts crude hydrocarbons into valuable fuel additives, such as alcohol fuel additives. This unique sequence can significantly improve the efficiency of the process, thereby reducing total capital costs. The final fuel additive products can have levels of 1-butanol, 2-butanol, tert-butyl alcohol, C4-dimer, or a combination thereof, for example, the final fuel additive products can have levels of the C4-dimer comprising trimethylpentane, di-isobutylene, 2,2,4 trimethylpentane, 2,3,3 trimethylpentane, or a combination thereof in an amount of 0.01 weight % to 50 weight %, based on the total weight of the fuel additive, high octane numbers (e.g., greater than or equal to 85 RON, or greater than or equal to 87 RON), and low Reid vapor pressures of greater than or equal to 55 Kilopascals. For example, the trimethylpentane can be present in an amount of 0.1 to 25 weight percent, for example, 1 to 20 weight %. Any one or all of these properties can correlate with high performance and high market value. The method disclosed herein can also produce secondary products along with the fuel additive product. For example, methyl tertiary butyl ether (MTBE) products can be produced along with the fuel additive, thus maximizing the efficiency and productivity of the process.

A system used in the method can include a methyl tertiary butyl ether synthesis unit that can handle a butadiene concentration up to an including 45% by weight to the isobutylene to produce methyl tertiary butyl ether with an external methanol stream. Such a product can be used as a fuel additive. A selective hydrogenation unit can be used to help achieve maximum increase in the production of 1-butene and 2-butene from butadiene present in the feed stream. For example, less than or equal to 10% by weight, for example, less than or equal to 5% by weight of butadiene can be left in the feed stream after conversion to 1-butene and 2-butene. The fuel additive can be made from, among other components, 1-butene and 2-butene together with a minimum amount (e.g., 0.1 to 15% by weight) of isobutylene. The method disclosed herein can provide two fuel additives, methyl tertiary butyl ether and another gasoline octane booster comprising mixed alcohols (i.e., C4 alcohols).

The method can include passing a feed stream of crude hydrocarbons through a MTBE unit producing a first process stream. The feed stream can first be cracked in a cracker unit to produce a cracked stream that is withdrawn from the cracker unit and passed into the MTBE unit. The MTBE unit can convert isobutylene present in the feed stream to a MTBE product. The first process stream can then be passed through a selective hydrogenation unit, e.g., a selective butadiene hydrogenation unit, to produce a second process stream. This selective hydrogenation unit can convert the butadiene present in the first process stream to 1-butene and 2-butene. For example, greater than or equal to 90% by weight of the butadiene present in the first process stream to 1-butene and 2-butene, for example, greater than or equal to 93%, for example, greater than or equal to 95%, for example, greater than or equal to 95%. The selectivity for 1-butene and 2-butene can be tuned by carbon monoxide injection as discussed in detail further herein.

Minimization of butadiene in the method can increase desirable product specifications, such as octane number. The second process stream can then be passed through a hydration unit to produce a fuel additive, for example, an alcohol fuel additive, such as a mixed alcohol fuel additive, such as a C4 alcohol fuel additive. A third process stream can also be produced in the hydration unit, which can be recycled through an additional hydrogenation unit, for example, a C4 hydrogenation unit or a total hydrogenation unit. A hydrogenated stream can be formed in the hydrogenation unit and recycled to a point prior to the MTBE unit, for example, recycled to the cracker unit, which can be a steam cracker unit. The present process can maximize product quality for a fuel additive product while also producing additional MTBE products in an efficient manner, where the MTBE products can also be used as fuel additives.

The method disclosed herein can include passing a feed stream through an olefin production unit, for example, a hydrocarbon cracking unit, for example, a catalytic and/or steam cracking unit, such that a source of the feed stream can include a product of an olefin cracking process and/or an olefin production process. The feed stream can comprise hydrocarbons, for example, C4 hydrocarbons. Additional hydrocarbons, for example, C2 and C3 hydrocarbons, can also be fed to the olefin production unit. The feed stream can then be withdrawn from the olefin production unit as a crude C4 hydrocarbon stream. The process stream produced by the olefin production unit can comprise propane, propylene, ethyl acetylene, vinyl acetylene, 1,3-butadiene, 1,2-butadiene, isobutylene, cis-2-butene, trans-2-butene, 1-butene, isobutane, n-butane, or a combination thereof. The total C4 olefin content of the feed stream when withdrawn from a steam cracking unit can be greater than or equal to 90% by weight and the feed stream can comprise greater than or equal to 40% by weight isobutylene. The total C4 olefin content of the feed stream when withdrawn from a fluid catalytic cracking unit can be greater than or equal to 50% by weight and the stream can comprise greater than or equal to 30% by weight isobutane.

A cracked stream withdrawn from the cracker unit can then be passed through a MTBE unit. Methanol can be fed through the MTBE unit via a methanol stream. The MTBE unit can convert isobutylene present in the cracked stream to a MTBE product. The cracked stream can be contacted with the methanol and a catalyst, for example, an acid-type ion-exchange resin catalyst, within the MTBE unit. Methanol and isobutylene can be present within the MTBE unit in a molar ratio of 1.0 mole of isobutylene to 0.05 moles to 10.0 moles of methanol, for example, one mole of isobutylene to 0.1 moles to 5.0 moles of methanol, for example, one mole of isobutylene to 0.5 moles to 2.0 moles of methanol. The MTBE product can be withdrawn from the MTBE unit via a MTBE product stream. The purity of the MTBE product can be greater than or equal to 90%. The conversion rate from isobutylene to MTBE within the MTBE unit can greater than or equal to 75%, for example, greater than or equal to 85%, for example, greater than or equal to 95%.

A first process stream can be withdrawn from the MTBE unit with reduced isobutylene content. For example, the first process stream exiting the MTBE unit can comprise less than or equal to 5% by weight isobutylene. A temperature within the MTBE unit can be 15° C. to 150° C., for example, 35° C. to 125° C. A pressure within the MTBE unit can be 500 kiloPascals to 2800 kiloPascals, for example, 1000 kiloPascals to 2000 kiloPascals, for example, 1500 kiloPascals. The MTBE unit can process a stream having the presence of butadiene in an amount of up to 45% by weight. This can be accomplished through process improvements and the insertion of chemicals in selected places in the scheme to avoid polymerization, as further described below.

The etherification of isobutylene can be carried out in two reaction stages: a) the first reactor consists of a Water Cooled Tubular Reactor (WCTR), and b) a second adiabatic reactor. The reaction can be carried out in liquid phase over sulfonic resin catalyst with feed flows upwards through the reactor tubes whereas the reaction mixture can enter at a pressure such as to assure that the mixture stays in the liquid phase also where the highest temperature is attained. The reaction can be carried out nearly isothermally and the reaction heat can be removed by circulating temperate water in co-current flow in a closed through the shell side of the reactors. The reaction product, leaving the reactor, can be sent to a fractionation tower where MTBE product can be recovered at the bottom. The polymerization inhibitor (e.g., a mixture of tert-butylcatechol (TBC) and methanol) can be injected in the reactors and tower overhead.

The first process stream exiting the MTBE unit can then be passed through a selective hydrogenation unit. For example, the hydrogenation unit can be a selective butadiene hydrogenation unit. The selective hydrogenation unit can convert butadiene present in the process stream to 1-butene and 2-butene, for example, cis-2-butene and trans-2-butene. The conversion rate from butadiene to 1-butene, cis-2-butene and trans-2-butene can be greater than or equal to 90% by weight of the butadiene to 1-butene and 2-butene, preferably greater than or equal to 93%, preferably, greater than or equal to 94%, more preferably, greater than or equal to 95%. Propylene, ethyl acetylene, and vinyl acetylene present in the first process stream can also undergo hydrogenation within the selective hydrogenation unit. The hydrogenation unit can comprise multiple reactors in series, for example, the hydrogenation unit can comprise three reactor stages. The first two reactor stages can convert butadiene present in the first process stream to 2-butene, cis-2-butene and trans-2-butene. The first two reactor stages can comprise a selective hydrogenation catalyst. For example, the hydrogenation catalyst can comprise palladium with an aluminum base. The hydrogenation catalyst can comprise platinum, rhodium, palladium, ruthenium, cobalt, nickel, copper, or a combination thereof. The catalyst can be the same for the first two reactor stages. Hydrogen can be injected into the first process stream prior to passing through the first reactor stage.

Final hydrogenation reaction of di-olefins to a desired product of mono-olefin can be achieved in the third reactor. Carbon monoxide can be injected into the third reactor to attenuate the catalyst and minimize the isomerization reaction from 1-butene to 2-butene. During normal operations, the desired carbon monoxide injection rate can be 2 parts per million of the feed stream to the third reactor. The rate can be increased if too much 1-butene is being lost to 2-butene. The first process stream can then be withdrawn from the selective hydrogenation unit. Operation conditions for the selective hydrogenation unit are shown in Table 1. Temperature is reported in degrees Celsius and pressure in pounds per square inch gage and kiloPascals.

TABLE 1

| Reactor | Temp ° C. | Pressure (psig) | Catalyst | Representative BD content at exit |
|---|---|---|---|---|
| 1st Reactor | 40-70 | 140-400 (965-2758 kPa) | Noble metal/ Alumina | 7% |
| 2nd Reactor | 50-60 | 140-400 (965-2758 kPa) | Noble metal/ Alumina | 1% |
| 3rd Reactor | 60-80 | 250-270 (1724-1862 kPa) | Noble metal/ Alumina | <0.01% |

The second process stream exiting the selective hydrogenation unit can then be passed through a hydration unit to produce a third process stream and a fuel additive, for example, an alcohol additive, for example, a mixed alcohols fuel additive, for example, a C4 alcohol fuel additive. The second process stream entering the hydration unit can comprise fess than or equal to 5% butadiene by weight, for example, less than or equal to 3%, for example, less than or equal to 1%. The fuel additive product can be withdrawn from the hydration unit via a product stream. Water can be fed to the hydration unit via a water stream. The hydration unit can comprise an oscillating baffle reactor, a fixed bed reactor, a membrane integrated reactor, or a combination thereof. The hydration unit can convert butene present in the second process stream to butanol. For example, greater than or equal to 0.1% by weight of the butene present in the feed stream can be converted to butanol within the hydration unit, for example, greater than or equal to 30% by weight, for example, greater than or equal to 50% by weight, for example, greater than or equal 90% by weight. The second process stream can be contacted with water and a catalyst within the hydration unit. For example, the catalyst can comprise phosphoric acid, hypophosphorous acid, an ion-exchange resin, sulfur, polystyrene, polymer, niobium oxide, or a combination thereof. Water and butene can be present within the hydration unit in a molar ratio of 1.0 mote of water to 1 mole to 20 moles of butene, for example, one mole of water to 5 moles to 10 moles of butene. A temperature within the hydration unit can be 30° C. to 250° C., for example, 100° C. to 200° C. A pressure within the hydration unit can be 500 kiloPascals to 20,000 kiloPascals, for example, 5000 kiloPascals to 10,000 kiloPascals, for example, 7500 kiloPascals.

The fuel additive product can comprise 1-butanol, 2-butanol, tert-butyl alcohol, C4-dimer, or a combination thereof, for example, the C4-dimer comprising trimethylpentane, di-isobutylene, 2,2,4 trimethylpentane, 2,3,3 trimethylpentane, or a combination thereof. The fuel additive product can comprise greater than or equal to 0.1% by weight trimethylpentane, for example, greater than or equal to 0.5% by weight, for example, greater than or equal to 0.1 by weight. In some instances, the fuel additive product can comprise 10% by weight to 20% by weight trimethylpentane. A research octane number of the fuel additive product can be greater than or equal to 80, for example, greater than or equal to 82, for example, greater than or equal to 85, for example, greater than or equal to 91, for example, greater than or equal to 95. A motor octane number can be greater than or equal to 70, for example, greater than or equal to 75, for example, greater than or equal to 80, for example, greater than or equal to 82, for example, greater than or equal to 85, for example, greater than or equal to 90, for example, greater than or equal to 95.

The octane number is a standard measurement used to gage the performance of an engine or fuel. The higher the octane number, the more compression the fuel is able to withstand before igniting. Fuels with higher octane ratings are generally used in high performance gasoline engines that need higher compression ratios. Fuels with lower octane numbers can be desirable for diesel engines because diesel engines do not compress the fuel, but rather compress only air and then inject fuel into the air which is heated by compression. Gasoline engines rely on ignition of air and fuel compressed together as a mixture, which is ignited at the end of the compression stroke using spark plugs. As a result, high compressibility of fuel is a consideration for gasoline engines.

The Research Octane Number is determined by running the fuel in a test engine at a speed of 600 revolutions per minute with a variable compression ratio under controlled conditions, and comparing the results with those for mixtures of iso-octane and n-heptane. Higher octane ratings can give higher amounts of energy needed to initiate combustion. Fuels with higher octane ratings are less prone to auto-ignition and can withstand a greater rise in temperature during the compression stroke of an internal combustion engine without auto-igniting.

Reid vapor pressure is used to measure the volatility of gasoline defined as the absolute vapor pressure exerted by a liquid at 37.8° C. as determined by ASTM D-323. The test measures the vapor pressure of gasoline volatile crude oil, and other volatile petroleum products, except for liquefied petroleum gases. Reid vapor pressure is measured in kiloPascals and represents a relative pressure to atmospheric pressure since ASTM D-323 measures the gage pressure of the sample in a non-evacuated chamber. High levels of vaporization are desired for winter starting and operation and lower levels are desirable in avoiding vapor lock during summer heat. Fuel cannot be pumped when vapor is present in the fuel line and winter starting will be difficult when liquid gasoline in the combustion chambers has not vaporized. This means that the Reid vapor pressure is changed accordingly by oil producers seasonally to maintain gasoline engine reliability.

The Reid vapor pressure of the fuel additive product can be less than or equal to 75 kiloPascals, for example, less than or equal to 55 kiloPascals, for example, less than or equal to 25 kiloPascals. The fuel additive product can also comprise less than or equal to 1% by weight impurities such as diene. For example, the fuel additive product can comprise less than or equal to 0.1% by weight of butylene dimers.

The third process stream can comprise 1-butene, 2-butene, isobutane, isobutylene, n-butane, or a combination thereof. The third process stream exiting the hydration unit can be passed through a hydrogenation unit, a C4 hydrogenation unit, to produce a hydrogenated stream wherein greater than or equal to 0.01% of any butene present in the third process stream is converted to butane within the hydrogenation unit, preferably wherein the amount of butane in the hydrogenated stream is greater than or equal to 90%.

In some embodiments, the hydrogenation unit is a total hydrogenation unit. The total hydrogenation unit converts C4 olefins into saturated hydrocarbons before recycling to steam cracker. Optionally, the hydrogenated stream can be recycled to a steam cracker unit and/or to the initial feed stream.

A more complete understanding of the components, processes, and apparatuses disclosed herein can be obtained by reference to the accompanying drawings. These FIGURES also referred to herein as "FIG.") are merely schematic representations based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood a numeric designations refer to components of like function.

Referring now to the FIGURE, this simplified schematic diagram represents a unit sequence 10 used in a method for producing fuel additives. The sequence 10 can include passing a first feed stream 12 comprising hydrocarbons through a hydrocarbon cracking unit 14. For example, the hydrocarbon cracking unit 14 can be a steam cracking and/or catalytic cracking unit.

A cracked process stream 16 can then be withdrawn from the cracking unit 14. The cracked process stream 16 can comprise crude hydrocarbons, for example, C4 hydrocarbons. The cracked process stream 16 can then be passed through a MTBE unit 18. Methanol can be fed through the MTBE unit 18 via stream 20. The MTBE unit 18 can convert isobutylene present in the second process stream 16 to a MTBE product 22 that can be withdrawn from the MTBE unit 18.

A first process stream 24 can then be withdrawn from the MTBE unit 18, wherein the first process stream 24 comprises a reduced isobutylene content. The first process stream 24 can then be passed through a selective hydrogenation unit 26. The hydrogenation unit 26 can be a selective butadiene hydrogenation unit and can comprise multiple reactors in series. The hydrogenation unit 26 can convert butadiene present in the stream 24 to 1-butene and 2-butene as previously described in detail herein.

A second process stream 28 can then be withdrawn from the hydrogenation unit 26 and passed through a hydration unit 30 to produce a fuel additive 46, such as an alcohol fuel additive. The fuel additive 46 can be withdrawn from the hydration unit 30. Water can be fed to the hydration unit 30 via stream 44.

A third process stream 32 can be withdrawn from the hydration unit 30 and recycled to the initial feed stream 12. Optionally, the third process stream 32 can be passed through a total hydrogenation unit 42, e.g., a C4 hydrogenation unit, prior to returning to the feed stream 12. A hydrogenated stream 48 can be produced in the hydrogenation unit 42. The total hydrogenation unit 42 can convert the 1-butene and 2-butene present in the third process stream 32 to n-butane and isobutane. The resulting hydrogenated stream 48 can then be combined with the feed stream 12. Optionally, the hydrogenated stream 48 can be sent to a cracking unit, such as a steam cracking unit.

The methods disclosed herein include(s) at least the following aspects:

Aspect 1: A method of producing a fuel additive, comprising: passing a feed stream comprising C4 hydrocarbons through a methyl tertiary butyl ether unit producing a first process stream; passing the first process stream through a selective butadiene hydrogenation unit transforming greater than or equal to 90% by weight of the butadiene to 1-butene and 2-butene, preferably greater than or equal to 93%, preferably, greater than or equal to 94%, more preferably, greater than or equal to 95% producing a second process stream; passing the second process stream through a hydration unit producing a third process stream and the fuel additive; passing the third process stream through a total hydrogenation unit producing a hydrogenated stream; and passing the hydrogenated stream to a cracker unit.

Aspect 2: The method of Aspect 1, wherein a source of the feed stream comprises a product of an olefin cracking process and/or an olefin production process.

Aspect 3: The method of any of the preceding aspects, wherein the feed stream comprises propane, propylene, ethyl acetylene, vinyl acetylene, 1,3-butadiene, 1,2-butadiene, isobutylene, cis-2-butene, trans-2-butene, 1-butene, isobutane, n-butane, or a combination thereof.

Aspect 4: The method of any of the preceding aspects, further comprising contacting the feed stream with a catalyst within the methyl tertiary butyl ether unit, wherein the catalyst comprises an acid-type ion-exchange resin.

Aspect 5: The method of any of the preceding aspects, wherein a temperature within the methyl tertiary butyl ether unit is 15° C. to 150° C. and a pressure within the methyl tertiary butyl ether unit is 500 kiloPascals to 2800 kiloPascals.

Aspect 6: The method of any of the preceding aspects, wherein methanol and isobutylene are present in the methyl tertiary butyl ether unit in a molar ratio of one mole of isobutylene to 0.1 mole to 5 moles of methanol.

Aspect 7: The method of any of the preceding aspects, wherein greater than or equal to 0.1% by weight of any isobutylene present in the feed stream is converted to methyl tertiary butyl ether within the methyl tertiary butyl ether unit.

Aspect 8: The method of Aspect 7, further comprising withdrawing a methyl tertiary butyl ether product from the methyl tertiary butyl ether unit.

Aspect 9: The method of any of the preceding aspects, wherein the second process stream comprises less than or equal to 5.0% by weight, preferably less than or equal to 3.0%, more preferably less than or equal to 1.0% by weight butadiene prior to passing through the hydration unit.

Aspect 10: The method of any of the preceding aspects, further comprising contacting the second process stream with a catalyst within the hydration unit, wherein the catalyst comprises phosphoric acid, hypophosphorous acid, ion-exchange resin, sulfur, polystyrene, polymer, niobium oxide, or a combination thereof.

Aspect 11: The method of any of the preceding aspects, wherein a temperature within the hydration unit is 30° C. to 250° C. and a pressure within the hydration unit is 500 kiloPascals to 20,000 kiloPascals.

Aspect 12: The method of any of the preceding aspects, wherein greater than or equal to 0.10% of any butene present in the second process stream is converted to butanol within the hydration unit, preferably 1% to 90% of any butadiene present in the second process stream is converted to butanol within the hydration unit.

Aspect 13: The method of any of the preceding aspects, further comprising withdrawing a fuel additive product from the hydration unit.

Aspect 14: The method of Aspect 13, wherein the fuel additive product comprises 1-butanol, 2-butanol, tert-butyl alcohol, di-isobutene, or a combination thereof.

Aspect 15: The method of Aspect 13, wherein a research octane number of the fuel additive product is greater than or equal to 80, preferably greater than or equal to 82, more preferably, greater than or equal to 85.

Aspect 16: The method of Aspect 13, wherein a Reid vapor pressure of the fuel additive product is less than or equal to 55 kiloPascals, preferably, less than or equal to 45 kiloPascals, more preferably, less than or equal to 35 kiloPascals, most preferably, less than or equal to 25 kiloPascals.

Aspect 17: The method of any of the preceding aspects, wherein greater than or equal to 0.01%, preferably greater than or equal to 90%, of any butene present in the third process stream is converted to butane within the hydrogenation unit.

Aspect 18: A method of producing a fuel additive, comprising: passing a feed stream comprising hydrocarbons through a cracker unit producing a cracked stream; passing the cracked stream through a methyl tertiary butyl ether unit to produce a first process stream, wherein methanol and isobutylene are present in the methyl tertiary butyl ether unit in a molar ratio of one mole of isobutylene to 0.1 mole to 5 moles of methanol; withdrawing a methyl tertiary butyl ether product from the methyl tertiary butyl ether unit; passing the first process stream through a selective butadiene hydrogenation unit to produce a second process stream; passing the second process stream through a hydration unit producing a third process steam, wherein a temperature within the hydration unit is 30° C. to 190° C., a pressure within the hydration unit is 500 kiloPascals to 20,000 kiloPascals, and wherein greater than or equal to 0.10% of any butene present in the third process stream is converted to butanol within the hydration unit; withdrawing a fuel additive product from the hydration unit, wherein the fuel additive product comprises 1-butanol, 2-butanol, tert-butyl alcohol, di-isobutene, or a combination thereof; passing the third process stream through a total hydrogenation unit producing a hydrogenated process stream; and recycling the hydrogenated process stream to a cracker unit.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like. In a list of alternatively useable species, "a combination thereof" means that the combination can include a combination of at least one element of the list with one or more like elements not named. Also, "at least one of" means that the list is inclusive of each element individually, as well as combinations of two or more elements of the list, and combinations of at least one element of the list with like elements not named.

All cited patents, patent applications, and other references are incorporated herein by reference in their entirety. However, if a term in the present application contradicts or conflicts with a term in the incorporated reference, the term from the present application takes precedence over the conflicting term from the incorporated reference While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method of producing a fuel additive, comprising:
   passing a feed stream comprising C4 hydrocarbons through a methyl tertiary butyl ether unit producing a first process stream and a methyl tertiary butyl ether product;
   passing the first process stream through a selective butadiene hydrogenation unit transforming greater than or equal to 90% by weight of butadiene in the first process stream to 1-butene and 2-butene, producing a second process stream;
   passing the second process stream through a hydration unit producing a third process stream and the fuel additive, wherein the second process stream comprises less than or equal to 5.0% by weight butadiene prior to passing through the hydration unit;
   passing the third process stream through a total hydrogenation unit producing a hydrogenated stream; and
   passing the hydrogenated stream to a cracker unit.

2. The method of claim 1, wherein a source of the feed stream comprises a product of an olefin cracking process and/or an olefin production process.

3. The method of claim 1, wherein the feed stream comprises at least one of propane, propylene, ethyl acetylene, vinyl acetylene, 1,3-butadiene, 1,2-butadiene, isobutylene, cis-2-butene, trans-2-butene, 1-butene, isobutane, or n-butane.

4. The method of claim 1, further comprising contacting the feed stream with a catalyst within the methyl tertiary butyl ether unit, wherein the catalyst comprises an acid-type ion-exchange resin.

5. The method of claim 1, wherein a temperature within the methyl tertiary butyl ether unit is 15° C. to 150° C. and a pressure within the methyl tertiary butyl ether unit is 500 kiloPascals to 2800 kiloPascals.

6. The method of claim 1, wherein methanol and isobutylene are present in the methyl tertiary butyl ether unit in a molar ratio of one mole of isobutylene to 0.1 mole to 5 moles of methanol.

7. The method of claim 1, wherein greater than or equal to 75% by weight of any isobutylene present in the feed stream is converted to methyl tertiary butyl ether within the methyl tertiary butyl ether unit.

8. The method of claim 1, further comprising withdrawing the methyl tertiary butyl ether product from the methyl tertiary butyl ether unit; and wherein the purity of the methyl tertiary butyl ether product is greater than or equal to 90%.

9. The method of claim 1, wherein the second process stream comprises less than or equal to 1.0% by weight butadiene prior to passing through the hydration unit.

10. The method of claim 1, further comprising contacting the second process stream with a catalyst within the hydration unit, wherein the catalyst comprises at least one of phosphoric acid, hypophosphorous acid, an ion-exchange resin, sulfur, polystyrene, a polymer, or niobium oxide.

11. The method of claim 1, wherein a temperature within the hydration unit is 30° C. to 250° C. and a pressure within the hydration unit is 500 kiloPascals to 20,000 kiloPascals.

12. The method of claim 1, wherein greater than or equal to 90% of any butene present in the second process stream is converted to butanol within the hydration unit.

13. The method of claim 1, further comprising withdrawing a fuel additive product from the hydration unit.

14. The method of claim 13, wherein the fuel additive product comprises at least one of 1-butanol, 2-butanol, tert-butyl alcohol, or a C4 dimer.

15. The method of claim 13, wherein a research octane number of the fuel additive product is greater than or equal to 80.

16. The method of claim 13, wherein a Reid vapor pressure of the fuel additive product is less than or equal to 55 kiloPascals.

17. The method of claim 13, wherein a research octane number of the fuel additive product is greater than or equal to 85; and
   wherein a Reid vapor pressure of the fuel additive product is less than or equal to 25 kiloPascals.

18. The method of claim 1, wherein greater than or equal to 90% of any butene present in the third process stream is converted to butane within the total hydrogenation unit.

19. The method of claim 1, wherein passing the first process stream through the selective butadiene hydrogenation unit transforms greater than or equal to 95% by weight of butadiene to 1-butene and 2-butene;
   wherein the second process stream comprises less than or equal to 1.0% by weight butadiene prior to passing through the hydration unit; and
   wherein greater than or equal to 90% of any butene present in the third process stream is converted to butane within the total hydrogenation unit.

20. A method of producing a fuel additive, comprising:
   passing a feed stream comprising hydrocarbons through a cracker unit producing a cracked stream;
   passing the cracked stream through a methyl tertiary butyl ether unit to produce a first process stream, wherein methanol and isobutylene are present in the methyl tertiary butyl ether unit in a molar ratio of one mole of isobutylene to 0.1 mole to 5 moles of methanol;
   withdrawing a methyl tertiary butyl ether product from the methyl tertiary butyl ether unit;
   passing the first process stream through a selective butadiene hydrogenation unit transforming greater than or equal to 90% by weight of butadiene in the first process stream to 1-butene and 2-butene, and producing a second process stream;
   passing the second process stream through a hydration unit producing a third process steam, wherein a temperature within the hydration unit is 30° C. to 190° C., a pressure within the hydration unit is 500 kiloPascals to 20,000 kiloPascals, and wherein greater than or equal to 90% of any butene present in the second process stream is converted to butanol within the hydration unit, and wherein the second process stream comprises less than or equal to 5.0% by weight butadiene prior to passing through the hydration unit;

withdrawing a fuel additive product from the hydration unit, wherein the fuel additive product comprises at least one of 1-butanol, 2-butanol, tert-butyl alcohol, or a C4 dimer;

passing the third process stream through a total hydrogenation unit producing a hydrogenated process stream; and recycling the hydrogenated process stream to a cracker unit;

wherein the fuel additive product comprises 1 to 25 weight percent trimethylpentane, and wherein the fuel additive product comprises less than or equal to 1% by weight diene impurities.

* * * * *